United States Patent [19]
Goldberg et al.

[11] Patent Number: 5,290,548
[45] Date of Patent: * Mar. 1, 1994

[54] SURFACE MODIFIED OCULAR IMPLANTS, SURGICAL INSTRUMENTS, DEVICES, PROSTHESES, CONTACT LENSES AND THE LIKE

[75] Inventors: Eugene P. Goldberg; Ali Yahiaoui; Khalid Mentak, all of Gainesville, Fla.

[73] Assignee: University of Florida, Gainesville, Fla.

[*] Notice: The portion of the term of this patent subsequent to Mar. 10, 2009 has been disclaimed.

[21] Appl. No.: 859,016

[22] Filed: Mar. 30, 1992

Related U.S. Application Data

[63] Continuation-in-part of Ser. No. 555,377, Jul. 19, 1990, Pat. No. 5,080,893, Ser. No. 592,478, Oct. 5, 1990, Pat. No. 5,108,776, Ser. No. 592,482, Oct. 5, 1990, Pat. No. 5,100,689, and Ser. No. 592,483, Oct. 5, 1990, Pat. No. 5,130,160, which is a continuation-in-part of Ser. No. 304,479, Feb. 1, 1989, Pat. No. 4,961,954, which is a continuation-in-part of Ser. No. 37,153, Apr. 10, 1987, Pat. No. 4,806,382.

[51] Int. Cl.⁵ ............. C08J 7/06; C08J 7/18; C08F 291/18; C08F 220/26; C08F 226/08; A61F 2/00; A61L 27/00; G02C 7/04

[52] U.S. Cl. .............. 424/78.18; 424/78.24; 522/84; 522/85; 522/149; 522/153; 522/912; 522/915; 525/937; 525/64; 264/1.4; 264/22; 427/495; 427/496; 427/506; 427/498; 427/532; 427/595; 427/294; 427/296; 427/299; 427/430.1; 623/11; 606/1

[58] Field of Search ............. 522/84, 85, 167, 153, 522/149, 912, 915; 525/937; 424/78.18, 78.24; 264/1.4, 2.2; 427/2, 42, 35, 36, 495, 496, 506, 498, 595

[56] References Cited

U.S. PATENT DOCUMENTS

4,589,964 5/1986 Mayhan et al. ............. 522/85
4,897,433 1/1990 Sugo et al. ............. 522/116

*Primary Examiner*—Edward Webman
*Attorney, Agent, or Firm*—Kerkam, Stowell, Kondracki & Clarke

[57] ABSTRACT

A method for modifying the plastic surface of an article adapted for contacting living tissue by the gamma or electron beam irradiation induced chemical graft coating thereon of:
(1) a neutral or ionic water-soluble, hydrophilic vinylic monomer or salt thereof;
(2) a mixture of at least two of said monomers, or
(3) a mixture of (1) or (2) with up to about 50%, by weight, based on the total monomer weight, of a member selected from the group consisting of N-vinylpyrrolidone, 2-hydroxyethyl-methacrylate, and mixtures thereof; so as to form a hydrophilic graft polymer coating on the surface.

17 Claims, 5 Drawing Sheets

FT·IR/ATR SPECTRUM FOR PMAA·g·PMMA
(PRESOAK IN 40% NVP/60°C/4 HRS, GRAFT IN 10% MAA/0.10 Mrad).

FIG. 1

FT-IR/ATR SPECTRUM FOR PMAA·g·PMMA
(PRESOAK IN 40% NVP/60°C/4 HRS, GRAFT IN 10% MAA/0.10 Mrad).

FIG. 2

XPS SPECTRUM FOR PAMPSA·g·PMMA
(PRESOAK IN 40% NVP/60°C/4 HRS, GRAFT IN 10% AMPSA/0.05 Mrad).

FIG. 3

FT·IR/ATR SPECTRUM FOR PAM·g·PMMA
(PRESOAK IN 40% NVP/60°C/4 HRS, GRAFT IN 10% AM/0.05 Mrad).

FIG. 4

FT·IR/ATR SPECTRUM FOR PDMA·g·PMMA
(PRESOAK IN 40% NVP/60°C/4 HRS, GRAFT IN 10% DMA/0.05 Mrad).

FIG. 5

XPS SPECTRUM FOR PAM·g·PMMA
(PRESOAK IN 40% NVP/60°C/4 HRS, GRAFT IN 10% AM/0.05 Mrad).

FIG. 6

XPS SPECTRUM FOR PDMA·g·PMMA
(PRESOAK IN 40% NVP/60°C/4 HRS, GRAFT IN 10% DMA/0.05 Mrad).

FIG. 7

FT-IR/ATR SPECTRUM FOR PEGMA-g-PMMA
(PRESOAK IN 40% NVP/60°C/4 HRS, GRAFT IN 10% PEGMA-1000 WITH 0.075 Mrad).

FIG. 8

XPS SPECTRUM OF (PSSA-co-PVP)-g-PMMA

FIG. 9

SURFACE MODIFIED OCULAR IMPLANTS, SURGICAL INSTRUMENTS, DEVICES, PROSTHESES, CONTACT LENSES AND THE LIKE

BACKGROUND OF THE INVENTION

1. Related Applications

This application is a continuation-in-part of application Ser. Nos. 07/555,377 filed Jul. 19, 1990 U.S. Pat. No. 5,080,893; 07/592,478 filed Oct. 5, 1990 U.S. Pat. No. 5,108,776; 07/592,482 filed Oct. 5, 1990 U.S. Pat. No. 5,100,689; and 07/592,483 filed Oct. 5, 1990 U.S. Pat. No. 5,130,160, which are continuations-in-part of application Ser. No. 07/304,479 filed Feb. 1, 1989, now U.S. Pat. No. 4,961,954 issued Oct. 9, 1990, which is a continuation-in-part of application Ser. No. 07/037,153 filed Apr. 10, 1987, now U.S. Pat. No. 4,806,382 issued Feb. 21, 1989.

2. Field of the Invention

The present invention relates to plastic surgical instruments, medical devices, prosthetic cardiovascular implants, implants for hard and soft tissue, ocular implants, contact lenses and the like and methods for improving the tissue contacting surfaces thereof.

3. Prior Art

Studies have shown that the surgical implantation of ocular implants such as intraocular lenses (IOL), etc., can result in the loss of significant corneal endothelial tissue unless great care is taken to ensure a lack of contact between the device and the endothelium. Most ocular implants are constructed of hydrophobic polymethylmethacrylate (PMMA) polymers because of their superior optical qualities, resistance to biodegradation, and the like. It has been found, however, that PMMA surfaces adhere to endothelial cells upon even casual contact and that separation of the surface therefrom results in a tearing away of the endothelial tissue adhered to the polymer surface. Similar adhesive interactions with other ocular tissues, i.e., the iris, can also cause adverse tissue damage. Other hydrophobic polymers which are used or have been proposed for use in ocular implants (i.e., polypropylene, polyvinylidene fluoride, polycarbonate, polysiloxane) also can adhere to ocular tissue and thereby promote tissue damage.

It is well documented in the prior art that a significant disadvantage inherent in PMMA IOLs resides in the fact that any brief, non-traumatic contact between corneal endothelium and PMMA surfaces results in extensive damage to the endothelium. See Bourne et al, Am. J. Ophthalmol., Vol. 81, pp. 482-485 (1976); Forster et al, Trans. Am. Acad. Ophthalmol. Otolaryngol., Vol. 83, OP-195-OP-203 (1977); Katz et al, Trans. Am. Acad. Ophthalmol. Otolaryngol., Vol. 83, OP-204-OP-212 (1977); Kaufman et al, Science, Vol. 198, pp. 525-527 (1977) and Sugar et al, Arch. Ophthalmol., Vol. 96, pp. 449-450 (1978) for a discussion of the problem associated with implant surface/endothelium contact.

Since it is extremely difficult to avoid any contact between implant surfaces and endothelium during surgical procedures and especially to other sensitive ocular tissues during implant life, i.e., the iris, ciliary sulcus, and the like, efforts have been undertaken to modify the PMMA ocular implant surfaces to reduce the tendency thereof to adhere to and damage corneal endothelium.

Ocular implant surfaces have been coated with various hydrophilic polymer solutions or temporary soluble coatings such as methylcellulose, polyvinylpyrrolidone (Katz et al, supra, and Knight et al, [Chem. Abs., Vol. 92:203547f (1980)], and the like, to reduce the degree of adhesion between the implant surfaces and tissue cells. While offering some temporary protection, these methods have not proven entirely satisfactory since such coatings complicate surgery, do not adhere adequately to the implant surfaces, become dislodged or deteriorate after implantation, dissolve away rapidly during or soon after surgery or may produce adverse post-operative complications. Moreover, it is difficult to control the thicknesses and uniformity of such coatings.

Yalon et al [Acta: XXIV, International Congress of Ophthalmology, ed. Paul Henkind (1983)] and Knight, et al, supra, have reported attempts to produce protective coatings on PMMA implant surfaces by gamma-radiation induced polymerization of vinylpyrrolidone thereon. Their efforts were not altogether successful, however, since their methods also presented problems in controlling the optical and tissue protective qualities of the coatings. Process conditions and parameters (i.e., monomer concentration solvent, dose and dose rate) were not specified. The resulting coatings were of poor quality and non-uniform mechanical stability.

In U.S. Pat. No. 4,806,382, issued Feb. 21, 1989, there are described improved methods for producing hydrophilic, gamma irradiation induced polymerized and chemically grafted coatings on ocular implants constructed of a variety of polymeric materials, which methods overcome the above-noted difficulties and disadvantages.

The invention described in that patent is predicated on the discovery of certain process conditions and parameters that produce thin hydrophilic gamma irradiation induced polymerized and chemically grafted coatings of N-vinyl-pyrrolidone (NVP) [PVP], copolymerized NVP and 2-hydroxyethylmethacrylate (HEMA) [P(NVP-HEMA)], or HEMA [PHEMA] and their copolymers, particularly with ionic comonomers on the surfaces of ocular implants constructed of materials including polymethylmethacrylate (PMMA) and of other process conditions and parameters which produce thin gamma irradiation induced graft PVP, P(NVP-HEMA), PHEMA or copolymer coatings on the surfaces of ocular implant articles constructed of materials including polypropylene (PP), polyvinylidene fluoride (PVDF), polycarbonate (PC) and polysiloxane or silicone (PDMSO). The coatings increase the hydrophilicity of the implant surface and minimize adhesion between the surface and sensitive ocular tissues such as corneal endothelium or iris, thereby minimizing tissue damage and post-operative complications occasioned by contact between the implant surface and ocular tissue. The coatings produced by the improved method of the invention described in U.S. Pat. No. 4,806,382 are thin and uniform. Moreover, they are chemically bound to the surface of the ocular implant and, therefore, far more durable and less subject to removal, degradation or deterioration during or following surgery than the coatings produced by prior art methods.

The improved gamma irradiation induced graft polymerization of NVP, HEMA or mixtures of NVP and HEMA on ocular implant surfaces comprising PMMA to form optimum PVP, P(NVP-HEMA) or PHEMA graft polymer surface modifications thereon described in U.S. Pat. No. 4,806,382 comprises carrying out the graft polymerization in an aqueous solution under specific combinations of the following conditions:

(a) monomer concentration in the range of from about 0.5 to about 50%, by weight;

(b) total gamma dose in the range of from about 0.01 to about 0.50 Mrad;

(c) gamma dose rate in the range of from about 10 to about 2,500 rads/minute; and (d) maintaining the molecular weight of the polymer in solution in the range of from about 250,000 to about 5,000,000.

The maintenance of the molecular weight of the polymer in solution at certain values, identified in U.S. Pat. No. 4,806,382, as a critical condition of the method is not actually a "condition" of the method, but rather, as stated in the specification, a result which is dependent on the reaction conditions employed in carrying out the graft polymerization process. It is, therefore, not appropriate to specify the molecular weight of the polymer in solution as a process "condition" since it is rather an outcome of the reaction conditions used in this invention and may be widely varied depending on specific gamma graft monomer-substrate-process conditions. If a certain set of fixed conditions are employed, namely: monomer, monomer concentration, total gamma dose, gamma dose rate, the molecular weight of the polymer formed in solution polymerization and radical inhibitors will be an output of the process which is dependent upon the values of the above-noted monomer, monomer concentration, total gamma dose, gamma dose rate polymerization and radical inhibitor conditions. For example, in the presence of certain ionic monomers, solvents or radical inhibitors, solution polymerization may be inhibited significantly without sacrificing efficient surface graft polymerization and the resulting solution polymer molecular weight may thereby be relatively low (i.e., as low as 5,000–10,000).

Since the application which matured into U.S. Pat. No. 4,806,382 was filed, the inventors of the subject matter defined therein conducted additional research and unexpectedly found that although relatively low doses of 0.01 to 0.20 Mrad are generally preferred for the compositions of this invention, the process could be conducted at a total gamma dose as low as 0.001 Mrad. This improved method is described in U.S. application Ser. No. 07/592,483 filed Oct. 5, 1990, now U.S. Pat. No. 5,130,160.

The state of the art prior to the application which matured into U.S. Pat. No. 4,806,382 taught the use of relatively high gamma doses, generally greater than 0.5 Mrad, for gamma polymerization grafting, and it was therefore surprising to find that surface grafting could be achieved at doses as low as 0.01 Mrad. The achievement of effective grafting at doses as low as 0.001 Mrad is consequently an even more unexpected result of the process of this invention. Furthermore, although grafting with monomer concentrations as low as 0.5 wt % was indicated in prior U.S. Pat. No. 4,806,382, further research has revealed that monomer concentrations as low as 0.1 wt % may be utilized in some embodiments of the graft process of this prior patent.

Optimally, the method may also be carried out under one or more of the following conditions:

(e) substantially excluding free oxygen from the aqueous graft polymerization solution;

(f) maintaining the thickness of the PVP or P(NVP-HEMA) surface graft in the range of from about 100 Å to about 150 microns;

(g) including a free radical scavenger in the aqueous graft polymerization solution; and (h) including in the aqueous graft polymerization solution a swelling solvent for PMMA or other polymer substrate surface.

The improved gamma irradiation induced graft polymerization of NVP, mixtures of NVP and HEMA, HEMA and other hydrophilic monomers or their copolymers on ocular implant surfaces comprising PP, PVDF, PC or PDMSO to form optimum PVP or P(NVP-HEMA) surface grafts thereon may also be carried out under specific combinations of the process parameters as indicated above for PMMA, but also under conditions which involve excluding free oxygen from the polymerization solution for preferred surface modification of these ocular implant polymer substrates.

At the present time, surgical instruments, medical devices, prosthetic implants, contact lenses and the like which are intended for contact with blood or with sensitive tissue surfaces are constructed of materials having the necessary physical properties to enable their use for the intended application; however, they suffer from the disadvantage that due to the generally hydrophobic nature of the blood or tissue contacting surfaces thereof, they exhibit undesired thrombogenic properties and, as noted for ocular implants, significant damage may occur to various fragile or sensitive tissues by adhesion and manipulation or movement on contact with these instruments.

In U.S. Pat. No. 4,961,954, there are described improved methods for producing hydrophilic, gamma irradiation induced polymerized and chemically grafted coatings on such instruments, devices and the like so constructed of a variety of polymeric materials.

The invention described in U.S. Pat. No. 4,961,954 is predicated on the discovery of certain process conditions and parameters that produce thin, hydrophilic, gamma or electron beam irradiation polymerized and chemically grafted coatings of N-vinylpyrrolidone (NVP [PVP]), copolymerized NVP and 2-hydroxyethylmethacrylate (HEMA) [P(NVP-HEMA)] or HEMA [PHEMA] on the surfaces of articles adapted for contact with living tissue of a human or non-human animal, e.g., surgical instruments, medical devices, prosthetic implants, contact lenses and the like constructed of a wide variety of plastic materials. For purposes of the following description of the present invention, the term "tissue" is intended to include blood as well as solid tissue surfaces.

The surface modifications or chemically grafted coatings of the invention increase the hydrophilicity of the article surfaces and minimize adhesion between the surface and sensitive tissues such as blood cells, vascular endothelium, peritoneum, pericardium, and the like, thereby minimizing tissue damage and complications occasioned by contact between the article and such tissues. The coatings produced are thin and reproducibly uniform. Moreover, they are chemically bound to the surface of the article and, therefore, are far more durable and less subject to removal, degradation or deterioration during or following utilization of the articles than the coatings produced by prior art methods.

The improved gamma irradiation induced graft polymerization of NVP, HEMA or mixtures of NVP and HEMA on plastic article surfaces to form optimum PVP, P(NVP-HEMA) or PHEMA graft polymer surface modifications thereon described in U.S. Pat. No. 4,961,954 comprises carrying out the graft polymerization in an aqueous solution under specific combinations.

As in the case of the earlier U.S. Pat. No. 4,806,382, it was also found that maintenance of molecular weight of the polymer in solution was not a "condition" of the process, but rather a result dependent upon reaction conditions.

Moreover, it was also found that although relatively low doses of 0.01 to 0.20 Mrad are generally preferred, the process can be conducted at a total gamma dose as low as 0.001 Mrad. The improved method is described in U.S. patent application Ser. No. 07/592,482 filed Oct. 5, 1990, now U.S. Pat. No. 5,100,689.

In U.S. application Ser. No. 07/592,478 filed Oct. 5, 1990, now U.S. Pat. No. 5,108,776, and U.S. Pat. No. 5,094,876, an improvement on the methods described in these earlier U.S. patents is disclosed. The inventions described in these applications are predicated on the discovery that the methods are significantly simplified and improved by pre-soaking the article surface to be coated in a first solution comprising the monomer prior to graft polymerizing the monomer onto the surface from a second solution of the monomer.

It is an object of the present invention to provide other improved compositions and methods for producing hydrophilic coatings on the surfaces of such articles.

SUMMARY OF THE INVENTION

The present invention is predicated on the development of a method and compositions for modifying a plastic surface of an article, the surface adapted for contact with living tissue of a human or non-human animal, by the gamma irradiation or electron beam induced polymerized chemically grafted coating thereon of:

(1) a neutral or ionic water-soluble, hydrophilic monomer or salt thereof;

(2) a mixture of the monomers; or (3) a mixture of (1) or (2) with up to about 50% by weight based on the total monomer weight of a member selected from the group consisting of N-vinylpyrrolidone, 2-hydroxyethylmethacrylate, and mixtures thereof; so as to form a hydrophilic graft polymer coating on the surface comprising:

conducting the gamma irradiation or electron beam induced graft polymerization in an aqueous solution under the following conditions:

(a) monomer concentration in the range of from about 0.1% to about 50% by weight;

(b) total gamma or electron beam dose in the range of from about 0.001 to less than about 0.50 Mrad; and (c) gamma dose rate in the range of from about 10 to about 2,500 rads/min. or electron beam dose rate equivalent to a gamma irradiation dose rate in the range of from about 10 to about $10^8$ rads/min.

The invention also includes articles produced according to the above-described method.

DETAILED DESCRIPTION OF THE INVENTION

The entire disclosures of U.S. Pat. Nos. 4,806,382, 4,961,954 and 5,094,876 as well as application Ser. Nos. 07/592,478, U.S. Pat. No. 5,108,776, 07/592,482, U.S. Pat. No. 5,100,689 and 07/592,483 U.S. Pat. No. 5,130,160 are incorporated herein by reference.

Yalon et al (supra) and Knight et al (supra) disclose gamma irradiation coatings on PMMA using N-vinylpyrrolidone (NVP) and 2-hydroxyethylmethacrylate (HEMA) and indicate poor dynamic (abrasive) protection of endothelium for these coatings. Dissolvable coatings of polyvinylalcohol (PVA) were regarded as optimal for intraocular lenses (IOLs) by Knight et al (supra) and commercial development of a PVA-coated IOL was attempted with unsatisfactory clinical results. The gamma polymerization surface modifications reported by Knight et al (supra) and Yalon et al (supra) were carried out under process conditions of monomer concentration, solvent, dose and dose rate which are not specified and which apparently yielded poor quality, readily abraded coatings. Conditions for producing useful permanent PVP or PHEMA coatings on PMMA IOLs or any other plastic surface are not taught in the prior art. Neither Knight et al, Yalon et al or the literature on gamma-graft polymerization of the past 30 years suggests the process conditions required to achieve the complicated requirements for useful coatings on plastics. These requirements include:

(a) Thin, permanent, optically clear (in the case of contact lenses) and uniform graft coatings. The literature generally discloses conditions which produce distortion and degradation of the substrate due to the use of high gamma-radiation does (>1 Mrad) and non-aqueous solvent media, and yield thick, cloudy, non-uniform coatings [e.g., Chapiro, Radiation Chemistry of Polymeric Systems, John Wiley and Sons, Inc., New York (1962); Henglein et al, Angew. Chem., Vol. 15, p. 461 (1958)].

(b) Long-term biocompatibility in vivo.

(c) Low contact angle (high wettability) for water or underwater air bubble (less than about 30°).

(d) Non-adherent to tissue (adhesive force to endothelium less than about 150 mg/cm$^2$).

(e) Non-damaging to endothelium (less than ca. 20% damage for in vitro contact tests).

(f) Measurable graft polymer surface modification by ESCA or FTIR analysis.

(g) Abrasion resistance by sliding (dynamic) friction testing showing no change in wetting (contact angle) and confirming before and after presence of polymer graft coating.

(h) Rapid hydration—change from dry state to wetted lubricous state on immersion in water (within five minutes).

Yalon et al (supra) disclose an in vitro technique for measuring endothelium damage. Results for PMMA were used to illustrate the method. Although it was noted that PVP coatings reduced cell damage with less damage at higher monomer concentrations, the conditions for the experiment (i.e., irradiation dose, dose rate, and the like) were not disclosed, nor were any of the critical process-product relationships indicated.

The improved process conditions and parameters of the invention described in the above-noted U.S. patents and applications which are necessary to produce useful polymers having a surface modified by gamma irradiation induced graft polymerization therein of PVP, P(NVP-HEMA) or PHEMA include: % monomer, gamma dose, dose rate, penetration time or swelling time of monomer into the substrate prior to polymerization and oxygen (air) degassing. Other optimal process conditions include catalysts, free radical scavengers, polymer swelling solvents and temperature. The solution polymer molecular weight and M.W. distribution, the % conversion and residual monomer, the graft polymer thickness and surface properties, and the like, are process results which can change markedly as the process variables change. For example, the surface modification achieved for PVP on polymer surfaces will be different when using 10% monomer and 0.1 Mrad if prepared at low dose rates since low dose rates (slower polymerization) favor higher molecular weights. Similarly, degassed oxygen-free reaction media result in improved grafts at much lower doses. The presence of free radical scavengers such as copper or iron salts or organic reducing agents (i.e., ascorbic acid) also greatly influences other process parameters, generally reducing solution polymer molecular weight and preventing solution gelation at high monomer concentrations.

The method of the present invention is particularly applicable for the surface modification of medical instruments, devices, implants, ocular implants and contact lenses formed from a variety of plastic materials including, for example, poly-acrylates and -methacrylates (i.e., polymethylmethacrylate, polyethyl acrylate, polybutyl methacrylate, etc.); polyolefins (polyethylene, polypropylene, polybutadiene); SBS (styrene-butadiene), ethylene-propylene copolymers; SE/BS (styrene-ethylene/butadiene), polycarbonates (PC), fluorocarbon polymers (i.e., polyvinylidene fluoride-PVDF, poly-tetrafluoroethylene-PTFE, polyperfluoroethylenepropylene-FEP, polysiloxanes), various aliphatic and aromatic polyurethanes, including polyurethane polyester or polyether block copolymers, polyvinylchloride and various polyesters including dacron PET (polyethyleneterephthalates). It will be understood by those skilled in the art that the method of the present invention is also applicable to mixtures, blends and copolymers of the above.

The hydrophilic graft polymer surface modifications of this invention are especially advantageous for intraocular lenses (anterior chamber, posterior chamber and phakic), but are also of great value in affording improved tissue protection and improved biocompatibility for other ocular implants, such as corneal inlays, keratoprostheses, epikeratophakia devices, glaucoma drains, retinal staples, scleral buckles, and the like.

Any instrument, device, implant, and the like constructed of one or more of the above materials may be surface modified according to the present invention to improve the tissue contacting characteristics of the surfaces thereof.

Plastic surgical instruments and implements such as probes, retractors, tissue and vessel separators, irrigation and aspiration tools, phacoemulsification tools, sponges, clamps, gloves, lens glides, positioning tools, forceps, insertion tools, staples, sutures, and the like, may be treated in accordance with the present invention.

Medical devices such as hard and soft contact lenses, intravenous and central venous catheters, laser and balloon angioplasty devices, vascular and heart devices (tubes, catheters, balloons), ventricular assists, blood dialysis components, blood oxygenators, ureteral/urinary devices (Foley catheters, stents, tubes and balloons), airway catheters (endotracheal and tracheostomy tubes and cuffs), mammary implants, enteral feeding tubes, wound drainage tubes, blood bags and blood tubing may also be beneficially treated in accordance with the method of the present invention.

Implants which may be modified according to the present invention include, for example, vascular grafts, soft and hard tissue prostheses (mammary, cranio/facial, tendons, joints), heart valves and artificial hearts.

Modification of these instruments, devices, implants, and the like, improve the surfaces thereof so as to improve blood compatibility and reduce tissue adhesion and tissue damage during surgical contact and manipulation. Moreover, the invention operates to reduce cell adhesion for reduced inflammation, reduce fibrous capsule formation for soft tissue implants, and reduce thrombogenicity for cardiovascular devices and prostheses. The invention also acts to reduce bacterial adhesion and thereby reduce the incidence of infection and further operates to reduce interfacial abrasion and friction which is of special value for joint and tendon prostheses.

Polyolefins and polyolefin/hydrocarbon block polymers are useful for constructing medical tubing, catheters, blood bags, sutures, and the like. Copolymers of the SBS, EP or SE/BS type may be thermoplastic elastomers which combine rubbery properties with extrudable or injection moldable processing properties. Surface modification of such materials according to the present invention is effective in changing the normal surface characteristics of these polymers from hydrophobic to hydrophilic.

The fluorocarbon polymers are widely used for catheters (i.e., intravenous catheters), for vascular protheses (i.e., vascular grafts) and for coating medical devices, instruments and implants due to their biocompatibility and inertness. However, the surface properties may be improved significantly according to the present invention to reduce cell and tissue adhesion and improve blood compatibility.

The silicone polymers are widely used for medical tubing and catheters, for mammary implants and other soft tissue prostheses. Hydrophilic surface modification, according to this invention, acts to reduce cell and tissue abrasion and adhesion and to thereby reduce fibrous capsule formation which is a major complication of soft tissue implants. Similarly, polyvinylchloride surface modification to produce more hydrophilic vinyl tubing and film surfaces can reduce thrombogenicity and improve biocompatibility of blood tubing, blood bags, catheters and other medical devices made of polyvinylchloride.

Polyurethanes which are used for such applications as pacer leads, intravenous catheters, enteral feeding tubes, vascular grafts, and the like, are also beneficially modified by the process and materials of this invention to produce more hydrophilic surfaces and make such devices more biocompatible.

Exemplary of suitable neutral or ionic water-soluble, hydrophilic monomers useful in the practice of the present invention are acrylamide, dimethylacrylamide, polyethylene glycol monomethacrylate, hydroxypropylacrylamide, methacrylic acid, sulfopropylacrylate, styrene-sulfonic acid, 2-acrylamide-2-methyl-1-propane sulfonic acid, vinylsulfonic acid, dimethylaminoethylmethacrylate and mixtures and salts thereof.

Each of the above-described process conditions and parameters of the method of the invention may be varied within the ranges discussed below to produce certain specific combinations which are particularly advantageous for the surface modification of a particular polymeric surface.

(a) Monomer concentration: Increasing monomer concentration increases polymer mol. wt. in the graft solution and reduces contact angle (C.A.), i.e., renders the surface more hydrophilic. For example, in the case of forming PVP coatings on PMMA, in the range of from about 3-15% NVP the PMMA graft C.A. decreases from 29° to 21° at 0.1 Mrad and 309 rads/min. However, this effect is sensitive to dose rate and total dose. For example, at 1-10% NVP, but at a lower dose rate of 64 rads/min., the C.A. decreases from 49° to 18°.

In general, monomer concentrations in the range of 0.1-50% are preferred depending on other parameters. Concentrations as low as 0.1 to 0.5% at low dose rates can yield hydrophilic surface grafts with C.A. below 30°-40° under conditions of this invention. At monomer concentrations greater than 20-30%, effective grafting without solution polymer gelation requires low doses and use of free radical scavengers. Monomer concentrations greater than 50% are feasible but not preferred since high concentrations of radical scavengers must be used and polymer mol. wts. and monomer conversion are lowered significantly by their use.

(b) Dose: In general, increasing total gamma dose reduces C.A. However, an important practical limit exists in that at higher doses, lower dose rates and higher monomer concentrations, reaction media become extremely viscous or form gels which are very difficult to wash and to remove (e.g., about 0.25 Mrad and 10% NVP at 309 rads/min).

It will be understood by those skilled in the art that electron beam radiation will also induce graft polymerization. Therefore, electron beam radiation of energies equivalent to that described herein for gamma radiation may be substituted for gamma radiation in the practice of the method of the invention. Electron beam voltages in the range of from about 50 KeV to about 10 MeV may be employed at currents of from about 5 mA to about 100 mA. For electron beam initiated polymerization grafting, conditions which produce dose rates substantially higher than for gamma graft polymerization, i.e., in the range of from about 10 to about $10^8$ rads/min or more may be employed.

(c) Dose rate: Decreasing the gamma radiation dose rate, e.g., generally increases solution polymer M.W. The C.A. also decreases correspondingly. As noted above, dose rates of up to $10^8$ rads/min or more are practical when employing electron beam irradiation.

(d) Solution Polymer Mol. Wt.: The mol. wt. may vary widely depending upon process conditions, monomers and radical inhibitors used. Effective grafting with low C.A. may therefore be achieved with even low mol. wt. solution polymer ($M_v$ as low as 5,000-10,000). However, solution polymer $M_v$ greater than 5,000,000 or gels which form during grafting are generally less practical because of washing problems.

(e) Degassing: Removal of oxygen from the graft solutions by a vacuum and/or an inert gas (e.g., argon purging) can have an important effect: lower total doses are required (practical grafting at less than 0.1 Mrad) and oxygen degassing can have a significant effect on $M_w$ and % conversion of monomer. For example, with degassing, good grafting of PVP on polypropylene (PP) is achieved at 0.05 Mrad and 10% NVP (C.A. 15°). Without degassing, little grafting occurs under these conditions. Oxygen degassing can be important to hydrophilic surface modification grafting where the substrate polymer is PP, PVDF or PDMS. It has been found that graft polymerization is inefficient when using these materials as substrates in the presence of oxygen. Oxygen degassing is also beneficial for PMMA and PC substrates in that much lower radiation doses (0.01-0.15 Mrad) become effective compared with grafting these polymers in the presence of oxygen.

(f) Graft thickness: Surface grafts less than 100-200 angstroms, although non-adhesive and hydrophilic, are useful but may exhibit somewhat less mechanical "softness" or compliant gel-like surfaces than thicker coatings for reduced tissue-contact trauma. Graft coatings greater than ca. 300-500 Å (or 0.03-0.05 microns) up to 50 microns or more are probably more desirable for many applications as long as they are smooth, uniform, optically clear for optic surfaces, and quickly hydrated.

Using no swelling solvents and no prolonged monomer contact with substrates prior to irradiation, surface grafts which exhibit desired properties under preferred process conditions have thicknesses of about 0.1 to 5 microns. However, using swelling solvents such as ethyl acetate with PMMA, polymer grafts of 100 microns or more can be prepared. For certain applications it may be preferred to have thicker "spongy" coatings of 20-200 microns.

(g) Free-Radical Scavengers: Free-radical traps, usually reducing agents such as $Cu^+$, $Fe^{+2}$, ascorbic acid, etc., are known to inhibit radical polymerization in solution and thus be effective (especially at high gamma doses, high dose rates and high monomer concentrations) in slowing the onset of solution gelation during grafting. However, under practical grafting conditions, this may result in lower solution polymer molecular weights and high concentrations of unreacted monomer. Use of metal salts may also be objectionable where maximum biocompatibility is critical.

Although most preferred graft conditions avoid the use of radical scavengers, useful conditions for graft coatings using the water-soluble, hydrophilic monomers of this invention have also been defined using ascorbic acid to limit high viscosity and gelation of the graft polymer solution. These conditions use high monomer concentrations (up to 50%) and thicker grafts are obtained using ethyl acetate as a swelling solvent (0.5-5%).

(h) Swelling solvents: The use of substrate polymer solvents in the aqueous monomer grafting solution facilitates swelling and monomer diffusion into the polymer before and during gamma polymerization. Penetration of monomers into the substrate increases graft coating thickness and enhances bonding to the surface. Solvents such as ethyl acetate have been shown to greatly facilitate this process with some substrates such as PMMA.

Although the above-described method represents a significant improvement over prior art methods, optimum results in each case depend upon the selection of a combination of numerous process parameters, monomers and conditions.

The foregoing hydrophilic polymer grafts and method are greatly simplified and the surface grafts are significantly enhanced by the method of the present invention according to which the substrate to be surface-modified is pre-soaked in a grafting monomer (or mixture of monomers) or in a first aqueous solution having a concentration of from about 5% to about 95%, by weight, of the grafting monomer (or mixture of monomers) for a period of time and at a temperature sufficient to facilitate diffusion of the monomers(s) into the substrate surface. This pre-soaking step avoids the necessity for utilizing organic swelling solvents. These swelling solvents can complicate the final coating procedure since they must be completely washed away and may promote crazing or cracking of the substrate polymers.

The monomer pre-soaking method of the present invention results in a controlled diffusion of monomer into the substrate and may often produce what may be regarded as an interpenetrating subsurface polymer structure for the ultimately formed hydrophilic polymer graft surface modification. The latter is rendered more durable by the thus formed anchoring substructure. This monomer pre-soak improvement is also beneficially conducted with mixed monomers wherein one hydrophilic monomer is used as the pre-soak monomer and a second hydrophilic monomer is used for the subsequent gamma polymerization grafting step. This is particularly advantageous, for example, with polysiloxane surface modification wherein a first monomer pre-soak of a monomer such as dimethylaminoethylmethacrylate followed by aqueous dimethylacylamide (DMA) present as the medium during gamma irradiation, results in a more stable, reproducible, hydrophilic surface for the highly flexible polysiloxane structure.

For substrates like PMMA, the pre-soaking is preferably conducted at a temperature of from about 25° C. to about 60° C. for from about 0.5 to about 24 hours or more (up to about 48 hours) using a first aqueous solution containing from about 5% to about 50%, by weight, of monomer(s) to achieve optimum diffusion thereof into the substrate.

Where the substrate surface is polypropylene (PP), polyvinylidene fluoride (PVDF), a polycarbonate (PC), a polysulfone (PSF) or a polysiloxane (PDMSO), the surface is preferably pre-soaked in the monomer(s) or a first aqueous solution containing from about 5% to about 95%, by weight, of monomer(s), at a temperature of from about 25° to about 90° C., and for from about 0.5 to about 24 hours or more (up to about 48 hours), to achieve maximum and optimum diffusion of the monomer(s) into the substrate surface.

Where mixtures of the neutral or ionic hydrophilic monomer with NVP and/or HEMA are employed to form graft copolymerized coatings, the mixtures may contain up to about 50%, by weight, of NVP, HEMA or mixtures thereof, based on the weight of the monomer mixture. However, above 20–30% HEMA, radical scavengers and low monomer concentrations should be used to prevent gelation since HEMA enhances the onset of gelation.

In general, choice of the "best" process will depend upon molecular structure of the substrate and grafting polymer and the coating thickness desired. In general, those conditions which produce extreme solution viscosities and gels or conditions which could produce solvent stress cracking or crazing of the substrates should be avoided. By way of example, the following process conditions are representative of practical conditions for the preparation of improved grafts using the monomers of this invention on various polymer substrates according to the method of this invention.

(a) For grafts on PP, PVDF and PDMSO (polydimethylsulfoxide), or combinations thereof, pre-soak the substrate in monomer at 60° C. for 4 hours followed by graft polymerization in 10% aqueous monomer with about 0.15 Mrad gamma radiation at about 500 rads/min. dose rate.

(b) For grafts on PMMA, PP, PVDF and PDMSO, or combinations thereof, pre-soak the substrate in 40% aqueous monomer at about 60° C. for 4 hours followed by graft polymerization in 10% aqueous monomer with about 0.15 Mrad gamma radiation at about 500 rads/min. dose rate.

c) For grafts on PMMA, PDMSO and PC, or combinations thereof, pre-soak the substrate in 40% aqueous monomer at about 60° C. for about 12 hours followed by graft polymerization in 10% aqueous monomer with about 0.15 Mrad gamma radiation at about 500 rads/min. dose rate.

All percentages expressed in the following non-limiting examples are by weight unless otherwise stated.

All contact angles (C.A.) and other surface characterizations for gamma or electron beam polymerization grafts, unless otherwise indicated, are for samples washed with water or water-alcohol at room temperature or elevated temperatures to remove soluble residual monomer and ungrafted polymer for the improved surface graft processes of this invention. The resulting graft polymers are stable and permanent for long-term implants and are not dissolved by aqueous media.

It will also be understood by those skilled in the art that the instruments, devices, and the like to be graft coated may be also constructed of materials other than PMMA, PP, PUR, PVC, PTFE, PVDF, PC or PDMS to facilitate their use. It will be understood by those skilled in the art that such materials may also be at least partially graft polymer surface modified so as to improve their properties. Structures of some neutral or ionic hydrophilic, water-soluble monomers useful in the practice of this invention are set forth below:

SSS

PEGMA

SVS

DMAEA

EXAMPLE 1

PVP (polyvinylpyrrolidone) grafts significantly reduce the incidence of abrasion damage to tissues such as ocular tissues, and reduce the adhesion and spreading of lens epithelial cells. Anionic surfaces, in addition to their hydrophilicity and good biocompatibility, exhibit superior anti-proliferative properties for epithelial cells and inhibit fibrosis. This example illustrates the improved gamma-induced graft polymerization of anionic vinyl monomers onto PMMA yielding surface compositions not previously prepared. Multi-component grafts involving combinations of anionic and neutral monomers of different functionalities have also been prepared. A range of suitable experimental conditions for each monomer or combination of monomers is illustrated.

Surface modification of PMMA involved graft copolymerization of methacrylic acid (MAA), sodium methacrylate (SMAA), N-vinylpyrrolidone (NVP), sodium vinylsulfonate (SVS), and sodium styrene sulfonate (SSS). MAA and NVP were purified by distillation at reduced pressure. SVS was recrystallized from methanol.

Pre-soaking when performed was carried out under various conditions of monomer concentration and composition, time and temperature as indicated in the tables. After presoaking, the substrates were transferred (if desired) to a lower monomer concentration, degassed by a vacuum and/or an argon purge, then exposed to gamma radiation from a $^{60}Co$ source. After radiation grafting, the samples were washed in distilled water. The samples were dried and surface characterization was carried out using contact angle measurements, XPS and gravimetric analysis.

TABLE 1

| Grafting Data for PMAA-g-PMMA. | | | |
|---|---|---|---|
| Pre-soaking Conditions | Grafting Conditions | % Graft | Contact Angle (water drop) |
| no pre-soak | 10% MAA 0.15 Mrad | 0.1 | 35° |
| 10% MAA @ 25° C., 12 hrs | 10% MAA 0.15 mrad | 1.8 | 32° |
| 10% MAA @ 25° C., 12 hrs | 10% MAA 0.1 Mrad | 0.9 | 32° |
| 40% NVP | 10% MAA | 1.2 | 31° |

TABLE 1-continued

| Grafting Data for PMAA-g-PMMA. | | | |
|---|---|---|---|
| Pre-soaking Conditions | Grafting Conditions | % Graft | Contact Angle (water drop) |
| @ 45° C., 4 hrs | 0.1 Mrad | | |

Dose rate = 701 rads/min.

TABLE 2

| Data for (PMAA-co-PVP)-g-PMMA. | | | | |
|---|---|---|---|---|
| % Monomer | | % | C.A. (air) | |
| MAA | NVP | Graft | (a) | (b) |
| 0.5 | 9.5 | 1.2 | 20° | 20° |
| 1.0 | 9.0 | 1.8 | 25° | 20° |
| 2.0 | 8.0 | 2.0 | 25° | 20° |

All samples were pre-soaked in 40% NVP at 55° C. for 3 hours prior to transferring to appropriate monomer or comonomer solution as indicated above. Total gamma dose was 0.075 Mrad @ 701 rads/min.
(a) before NaOH treatment;
(b) after NaOH treatment

TABLE 3

| Data for PSMAA-g-PMMA. | |
|---|---|
| % SMAA | C.A. (air) |
| 10 | 30° |
| 15 | 30° |
| 20 | 30° |
| 30 | 32° |

All samples were pre-soaked in 10% SMAA at 25° C. for 12 hrs. prior to gamma irradiation. Total radiation dose was 0.15 Mrad @ 701 rads/min.

TABLE 4

| Data of Polyvinylpyrrolidone-co-poly(sodium methacrylate)-g-PMMA. | | | | |
|---|---|---|---|---|
| % Monomer | | % | C.A. | Pre-soak |
| SMAA | NVP | Graft | (air) | Conditions |
| 1 | 9 | ≦0.1 | 20° | (a) |
| 5 | 5 | ≦0.1 | 31° | (a) |
| 5 | 10 | ≦0.1 | 30° | (a) |
| 10 | 10 | ≦0.1 | 25° | (a) |
| 10 | 20 | ≦0.1 | 30° | (a) |
| 10 | 20 | 6.3 | 28° | (b) |

Pre-Soak Conditions:
(a) 12 hrs. @ 25° C. in the same monomer composition, prior to gamma irradiation.
(b) 4 hrs. @ 60° C. in 40% NVP, then transfer to a different monomer composition as in previous case (a), prior to gamma irradiation.
Radiation Dose:
0.15 Mrad @ 701 rads/min. for all samples.

TABLE 5

| Data for Polyvinylpyrrolidone-co-poly (sodium methacrylate)-co-poly(sodium styrene sulfonate)-g-PMMA. | | | | |
|---|---|---|---|---|
| % Monomer | | | % | C.A. |
| NVP | SMAA | SSS | Graft | (air) |
| 10 | 10 | 10 | <0.1[a] | 28° |
| 10 | 10 | 10 | 2.5[b] | 26° |

[a]Pre-soak @ 25° C. for 12 hrs. in 10% NVP/10% SMAA/10% SSS, then irradiate in same monomer composition to 0.15 Mrad @ 701 rads/min.
[b]Pre-soak in 40% NVP @ 60° C. for 4 hrs., then transfer to 10% NVP/10% SMAA/10% SSS and irradiate to 0.15 Mrad @ 701 rads/min.

TABLE 6

| Data for Polyvinylpyrrolidone-co-poly-(sodium vinyl sulfonate)-co-poly(sodium methacrylate)-g-PMMA. | | | | |
|---|---|---|---|---|
| % Monomer | | | % | C.A. |
| NVP | SVS | SMAA | Graft | (air) |
| 13 | 1 | 1 | 0.1[a] | 35° |
| 13 | 1 | 1 | 0.2[b] | 35° |
| 13 | 1 | 1 | 0.2[c] | 27° |

TABLE 6-continued

Data for Polyvinylpyrrolidone-co-poly-(sodium vinyl sulfonate)-co-poly(sodium methacrylate)-g-PMMA.

| % Monomer | | | % | C.A. |
|---|---|---|---|---|
| NVP | SVS | SMAA | Graft | (air) |
| 13 | 1 | 1 | 1.5$^d$ | 27° |

$^a$no pre-soak.
$^b$pre-soak @ 25° C. for 24 hrs. and gamma irradiate in same monomer solution.
$^c$pre-soak @ 60° C. for 4 hrs. and gamma irradiate in same monomer solution.
$^d$pre-soak in 40% NVP @ 60° C. for 4 hrs., then transfer to 10% NVP/10% SVS/10% SMAA prior to gamma radiation.
Dose rate = 701 rads/min.

EXAMPLE 2

Some monomers do not graft polymerize readily under low dose radiation conditions. The "pre-soak method" was found to facilitate graft polymerization of sulfonated vinyl monomers (KSPA and AMPSA), as well as other vinyl monomers (AM, DMA, PEGMA). This example further illustrates more efficient graft surface modification using an initial monomer pre-soak.

TABLE 7

Data for PMAA-g-PMMA.

| Pre-soak Conditions | Graft Conditions | Graft Yield (wt. %) | Contact Angle |
|---|---|---|---|
| no pre-soak | 10% MAA 0.15 Mrad | ≦0.1 | 50° |
| 10% MAA @ 25° C., 12 hrs | 10% MAA 0.15 Mrad | 1.8 | 32° |
| 10% MAA @ 25° C., 12 hrs | 10% MAA 0.1 Mrad | 0.3 | 32° |
| 40% NVP @ 60° C., 4 hrs | 10% MAA 0.1 Mrad | 1.2 | 31° |
| 8% MAA @ 25° C., 12 hrs | 8% MAA 0.15 Mrad | 0.2 | 35° |

Dose rate = 701 rads/min.

Figure 1:
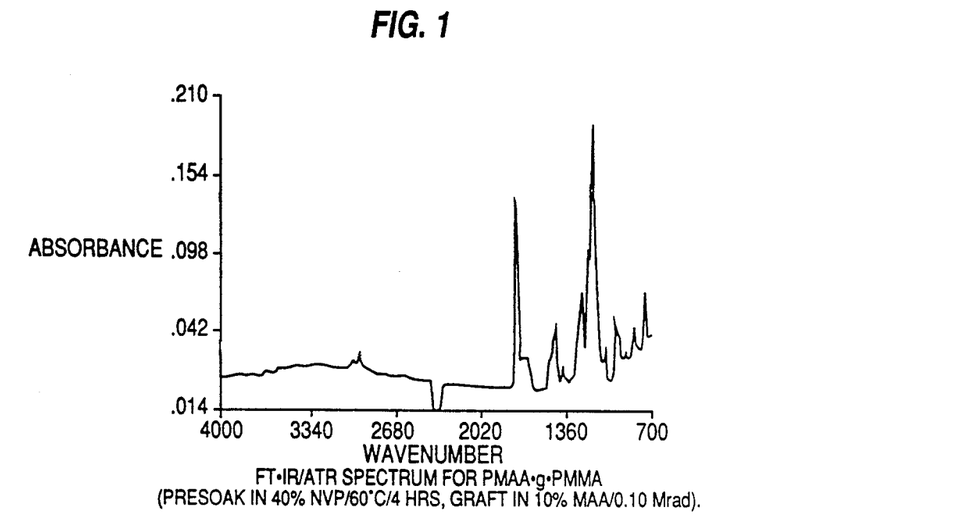
FIGS. 1-9 are graphical depictions of various spectra of the graft polymerized coatings of the invention verifying the structures of the various polymers.

FIG. 1 shows the FTIR/ATR spectrum for a PMAA-g-PMMA graft. An additional PMAA carbonyl peak appears as a shoulder to the ester carbonyl of PMMA.

TABLE 8

Data for (PMAA-co-PVP)-g-PMMA (dose = 0.1 Mrad). (Pre-soak in 40% NVP/60° C./4 hrs.)

| Monomer MAA/NVP$^{(a)}$ | Graft Yield (Wt. %) | Contact Angle | |
|---|---|---|---|
| | | (b) | (c) |
| 1/20 | 1.2 | 20° | 20° |
| 1/10 | 1.8 | 25° | 20° |
| 1/5 | 2.0 | 30° | 20° |

Dose rate = 701 rads/min.
$^{(a)}$[MAA-co-NVP] = 10 Wt. % overall
$^{(b)}$contact angle before NaOH treatment
$^{(c)}$contact angle after NaOH treatment

EXAMPLE 3

Sodium methacrylate (SMAA) does not readily graft polymerize on PMMA at low doses. Copolymerization of SMAA and NVP was found to improve graft polymerization with SMAA under low dose conditions.

TABLE 9

Data for (PSMAA-co-PVP)-g-PMMA

| Monomer SMAA-NVP | Overall Monomer Wt. % | Graft Yield (Wt. %) | Contact angle (°) |
|---|---|---|---|
| 1:10 | 10 | ≦0.1 | 20$^a$ |
| 1:1 | 10 | ≦0.1 | 31$^a$ |
| 1:2 | 15 | ≦0.1 | 40$^a$ |
| 1:2 | 30 | 6.3 | 28$^b$ |

Dose rate = 701 rads/min.
Radiation dose = 0.15 Mrad
$^a$with no pre-soak and
$^b$with pre-soak.

Although KSPA polymerizes readily with gamma radiation, its graft polymerization on hydrophobic substrates is more difficult to achieve than on a hydrophilic surface, probably because of high interfacial energy at the substrate-solution interface. Using 20% KSPA and 0.15 Mrad, a contact angle of 45° was obtained for PMMA surface modification. Using the pre-soak conditions of the NVP/PMMA grafting system (i.e., 40% NVP/60° C./4 hrs.), graft yield is significantly enhanced. As noted in the following tabulated data, the contact angle (21°) indicates that a highly hydrophilic surface is obtained.

TABLE 10

Data for KSPA-g-PMMA with Pre-soak.

| Pre-soaking @ 60° C. | | Grafting Wt. % KSPA | Graft Yield (Wt. %) | Contact Angle (°) |
|---|---|---|---|---|
| Monomer | t (hrs) | | | |
| 20% KSPA | 6 | 15 | ≦0.1 | 50 |
| 40% KSPA | 4 | 15 | ≦0.1 | 25 |
| 40% KSPA | 4 | 10 | ≦0.1 | 45 |
| 40% KSPA | 12 | 10 | 0.8 | 25 |
| 40% NVP | 4 | 10 | 2.1 | 21 |

Dose rate = 701 rads/min.

EXAMPLE 4

Figure 2:
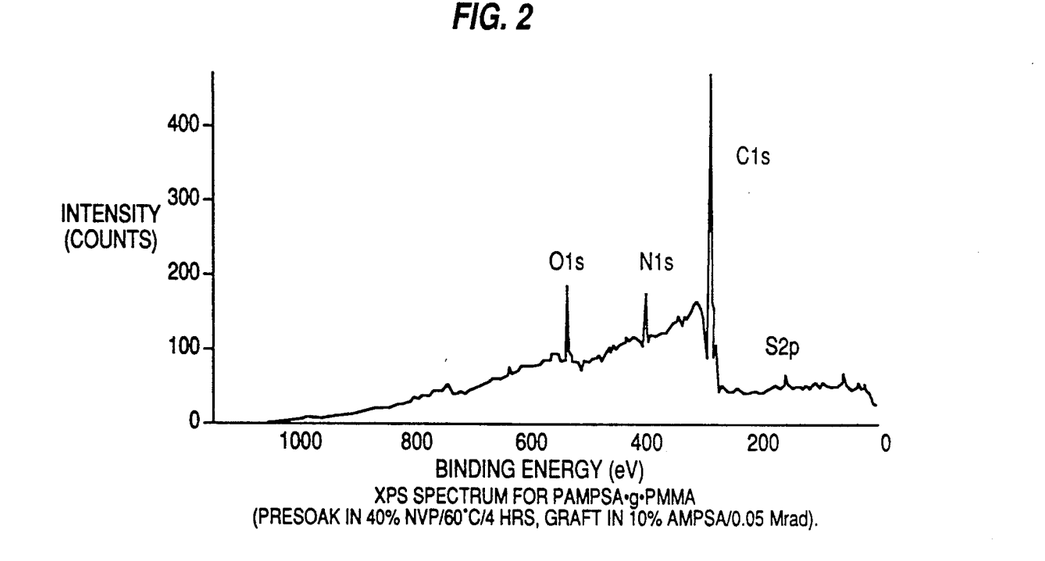

According to gravimetric analysis and contact angle measurements, improved grafting of AMPSA is achieved when the substrate is pre-soaked in 40% NVP at 60° C. for 4 hours, prior to gamma irradiation in a 10% AMPSA solution. XPS analysis (FIG. 2) provides evidence that PAMPSA is effectively grafted on PMMA by the appearance of S2p, N1s peaks in appropriate relative intensities, consistent with the elemental stoichiometry of PAMPSA.

TABLE 11

Data for AMPSA-g-PMMA.

| Pre-soaking @ 60° C. | | Grafting | | Graft Yield (Wt. %) | Contact Angle (°) |
|---|---|---|---|---|---|
| Monomer | t (hrs) | Wt. % AMPSA | Dose (Mrad) | | |
| 10% AMPSA | 6 | 10 | 0.05 | ≦0.1 | 50 |
| 20% AMPSA | 4 | 10 | 0.05 | ≦0.1 | 45 |
| 40% NVP | 4 | 10 | 0.05 | 1.3 | 21 |

Dose rate = 701 rads/min.

EXAMPLE 5

Figure 3:
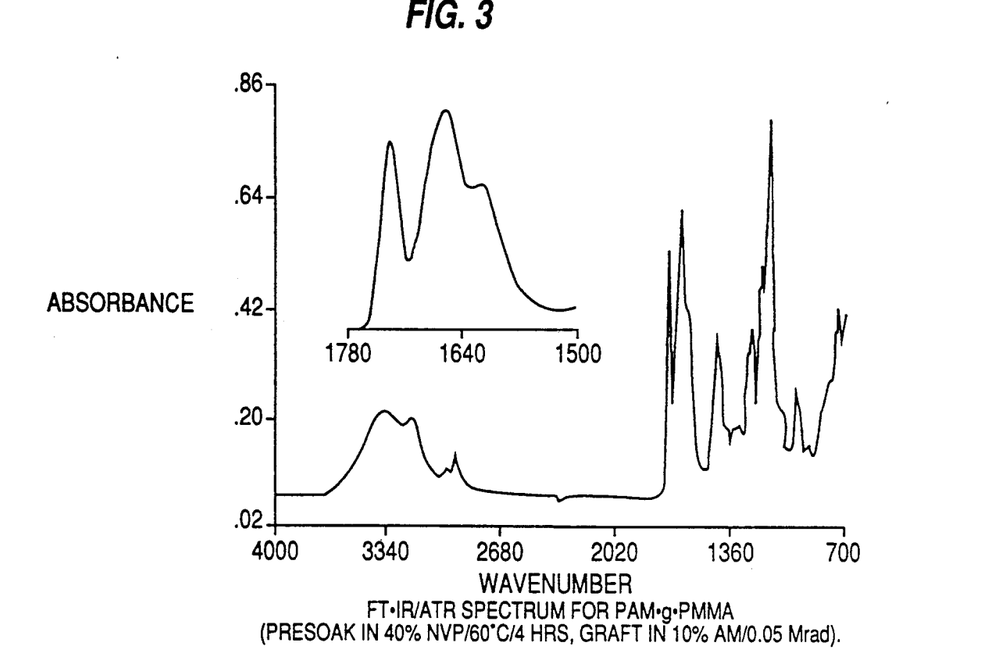
Figure 4:
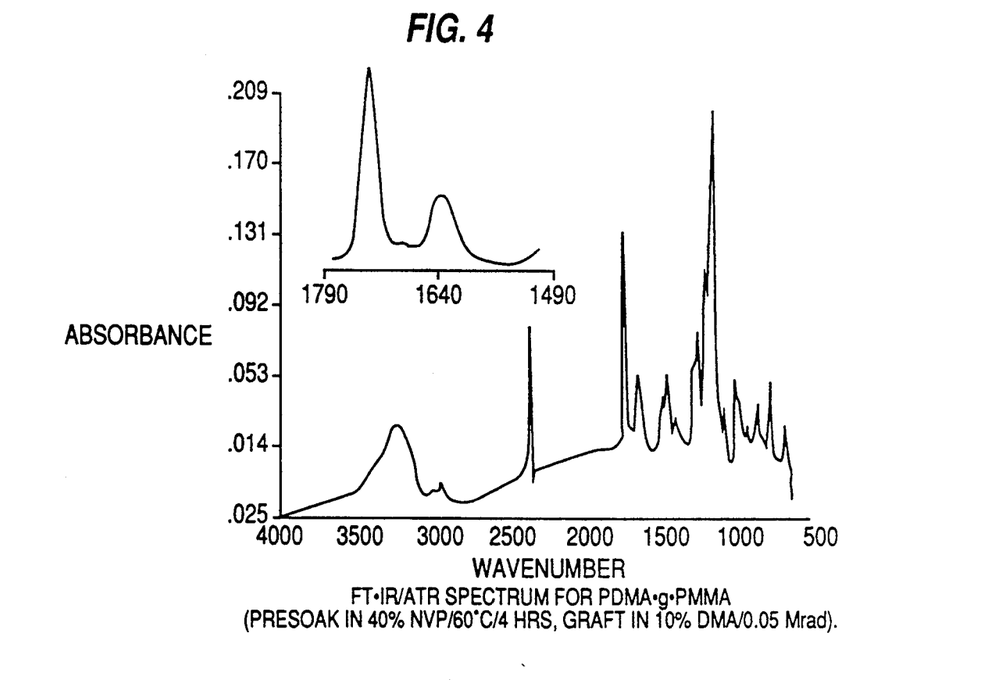

Although polymerization in solution is relatively easy, a problem with radiation grafting of AM and DMA is the early onset of solution homopolymerization. Changing the interface by lowering the energy barrier for monomer diffusion to the surface of the substrate has also been found to facilitate improved radiation grafting of AM and DMA on various hydrophobic substrates such as PMMA. Thus, pre-soaking in NVP at 60° C. for 4 hrs. prior to irradiation improved grafting of AM and DMA. Good evidence for AM grafting on PMMA is from FTIR/ATR analysis (FIG. 3), which shows a strong carbonyl peak at 1660 cm$^{-1}$, and another peak at 1550 cm$^{-1}$ which appears as a shoulder on the carbonyl peak. The 1550 cm$^{-1}$ adsorption band arises from coupling to the N—H bending and C—N stretching vibrations. In addition, a strong broad adsorption due to —NH$_2$ stretching is observed around 3350 cm$^{-1}$. Similarly, the FTIR/ATR spectrum of PDMA-g-PMMA (FIG. 4) also exhibits a strong absorption around 1640 cm$^{-1}$ due to the tertiary amide group of PDMA.

Figure 5:
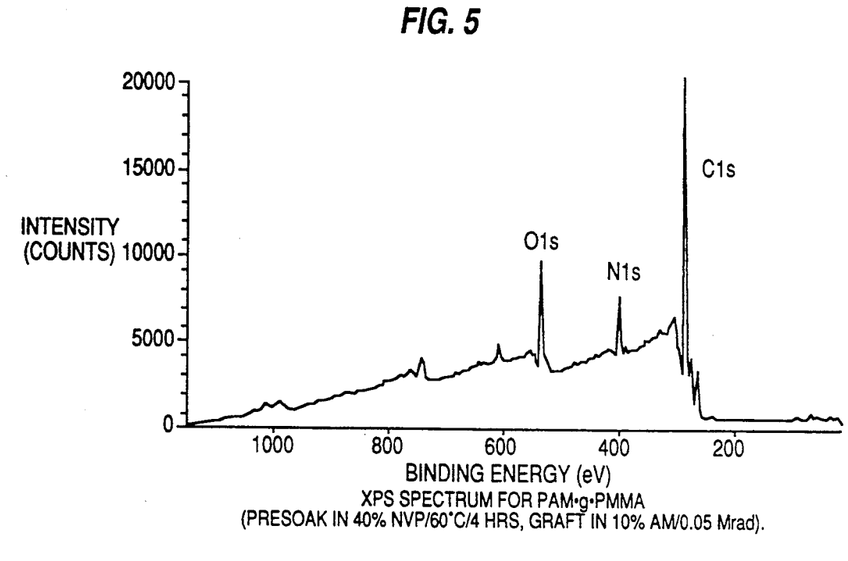
Figure 6:
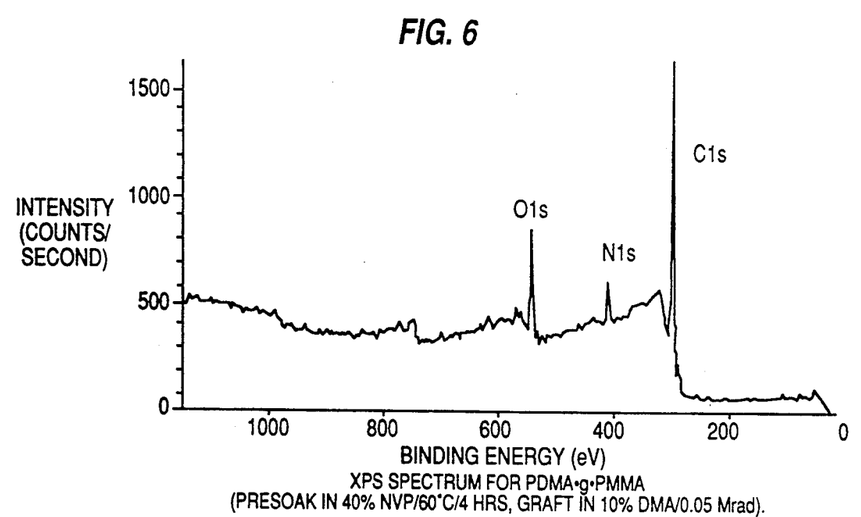

Both PAM-g-PMMA and PDMA-g-PMMA surfaces also exhibit relatively strong N1s peaks by XPS analysis (FIGS. 5 and 6) characteristic of these N-containing surface modifications.

TABLE 12

Data for Grafting of AM and DMA on PMMA with NVP Pre-soak.

|  | Dose (Mrad) | Contact Angle (°) | Graft Yield (Wt. %) | XPS (atom % N1s) |
|---|---|---|---|---|
| 10% AM | 0.05 | 18 | 2.5 | 8.8 |
| 10% DMA | 0.05 | 20 | 1.9 | 6.4 |

Dose rate = 701 rads/min.
Pre-soak was in 40% NVP/60° C./4 hrs.

EXAMPLE 6

Polyethylene glycol (PEG) is a neutral hydrophilic polymer having reportedly good blood and tissue biocompatibility. Radiation-induced graft polymerization of a vinyl functionalized PEG, methoxypolyethylene glycol monomethacrylate (PEGMA) was found to surface modify various polymers such as PMMA and other polymers described in this invention by both one-step radiation grafting and by the pre-soak method. PEGMA of various PEG molecular weights (i.e., 500 to 10,000 Daltons) are especially useful for grafting. PEGMA-1000 corresponding to 1000 MW PEG chains was used for this example.

TABLE 13

Gamma Radiation-Induced Grafting of PEGMA-1000 on PMMA.

| PEGMA (Wt. %) | Pre-Soak Time (hrs.) | Dose (Mrad) | Contact Angle |
|---|---|---|---|
| 5 | 0 | 0.15 | 52° |
| 5 | 2 | 0.15 | 40° |
| 5 | 4 | 0.15 | 39° |
| 5 | 12 | 0.15 | 34° |

Dose rate = 701 rads/min.
Samples were pre-soaked in grafting solutions at 25° C.

TABLE 14

Grafting of PEGMA-1000 on PMMA with NVP Pre-soaking.

| Pre-soak Conditions | PEGMA (Wt. %) | Dose (Mrad) | Contact Angle |
|---|---|---|---|
| (a) | 10 | 0.075 | 24° |
| (a) | 5 | 0.15 | 23° |
| (b) | 10 | 0.075 | 31° |

Dose rate = 701 rads/min.
Pre-soak conditions:
(a) 40% NVP/60° C./4 hrs.
(b) 10% PEGMA/60° C./4 hrs.

Figure 7:
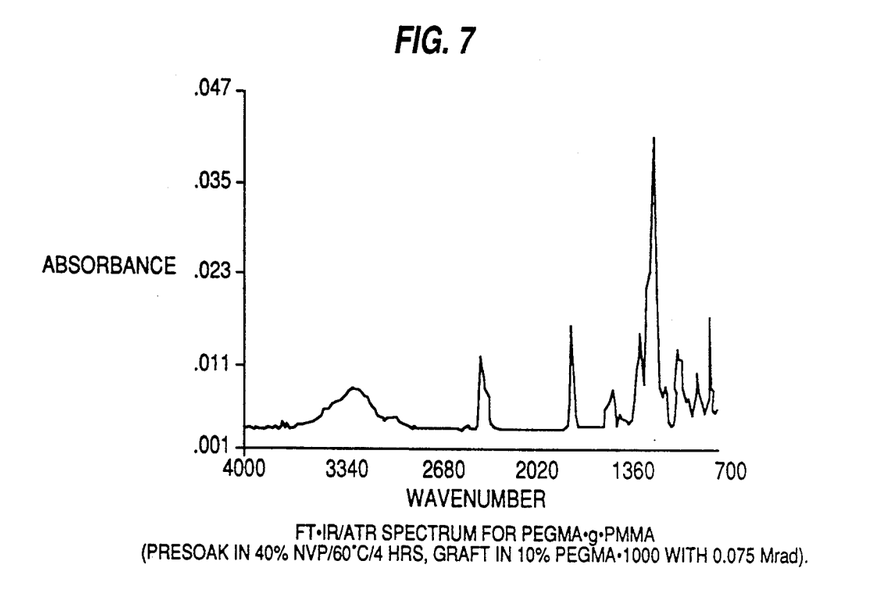

FIG. 7 shows a typical FTIR/ATR spectrum for PEGMA-g-PMMA. The expected IR absorption for PEGMA is in the 1000-1200 cm$^{-1}$ region for the ether group and the ether peak in the 1100 cm$^{-1}$ region is significantly more intense than the ester peak at 1725 cm$^{-1}$. FTIR/ATR also provides clear evidence that PEGMA is effectively grafted on PMMA.

EXAMPLE 7

Grafting of PSSA-co-PVP onto silicone (PDMS) was accomplished using SSA and NVP as comonomers to yield well characterized polysiloxane surface modifications. PDMS samples were sonicated twice in ethanol for 45 minutes, then vacuum dried @ 60° C. for 5 hours. Monomer concentrations were varied from 40% to 25% with different ratios of SSA to NVP. Samples were argon degassed prior to irradiation. Radiation does ranged from 0.05 Mrad up to 0.2 Mrad (dose rate 701 rads/min).

Pre-soaking was carried out in 100% NVP @ 25° C. for 24 hours. Very hydrophilic grafts were obtained and were characterized by air bubble contact angle and XPS analysis.

TABLE 15

Grafting Data for Non-presoaked Samples.

| Dose (Mrad) | % SSA | % NVP | C.A. (Air) |
|---|---|---|---|
| 0.05 | 20 | 20 | 17° |
| 0.05 | 20 | 10 | 16° |
| 0.05 | 20 | 5 | 14° |
| 0.1 | 20 | 20 | 15° |
| 0.1 | 20 | 10 | 19° |
| 0.1 | 20 | 5 | 17° |

TABLE 16

Grafting Data for Samples Pre-soaked in 100% NVP @ 25° C. for 24 hours

| Dose (Mrad) | % SSA | % NVP | C.A. (Air) |
|---|---|---|---|
| 0.05 | 20 | 20 | 13° |
| 0.05 | 20 | 10 | 12° |
| 0.05 | 20 | 5 | 15° |
| 0.1 | 20 | 5 | 12° |

EXAMPLE 8

Radiation graft copolymerization of SSA/NVP on PMMA and other polymer substrates is readily accomplished by the process of this invention. PMMA samples are ultrasonically cleaned twice in 0.1 Triton X-100/distilled water for 30 minutes and 4 times with distilled water for 20 minutes, then vacuum dried at 60° C. for 10 hours. Styrene sulfonic acid (SSA) sodium salt and NVP, distilled at reduced pressure, are used as comonomers (NVP/SSA ratio of 1:1) in water; total monomer concentration is 30%. Radiation dose and pre-soaking time in the comonomer solution at room temperature are varied. XPS shows grafting and contact angles less than 30° are obtained.

EXAMPLE 9

Anionic poly(styrenesulfonic acid) (PSSA) grafts are prepared on PMMA. PMMA slabs are sonicated twice in 0.1% aqueous Triton X-100 for 30 minutes and 4 times in distilled water for 20 minutes and then vacuum dried at 60° C. for at least 10 hours. The aqueous monomer solutions used for radiation grafting are: 20% SSA, 30% SSA/NVP (ratio of 2:1), 40% SSA/NVP (ratio of 1:1). Samples are argon degassed prior to irradiation. Radiation dose is 0.15 Mrad (dose rate 701 rads/min).

Figure 9:
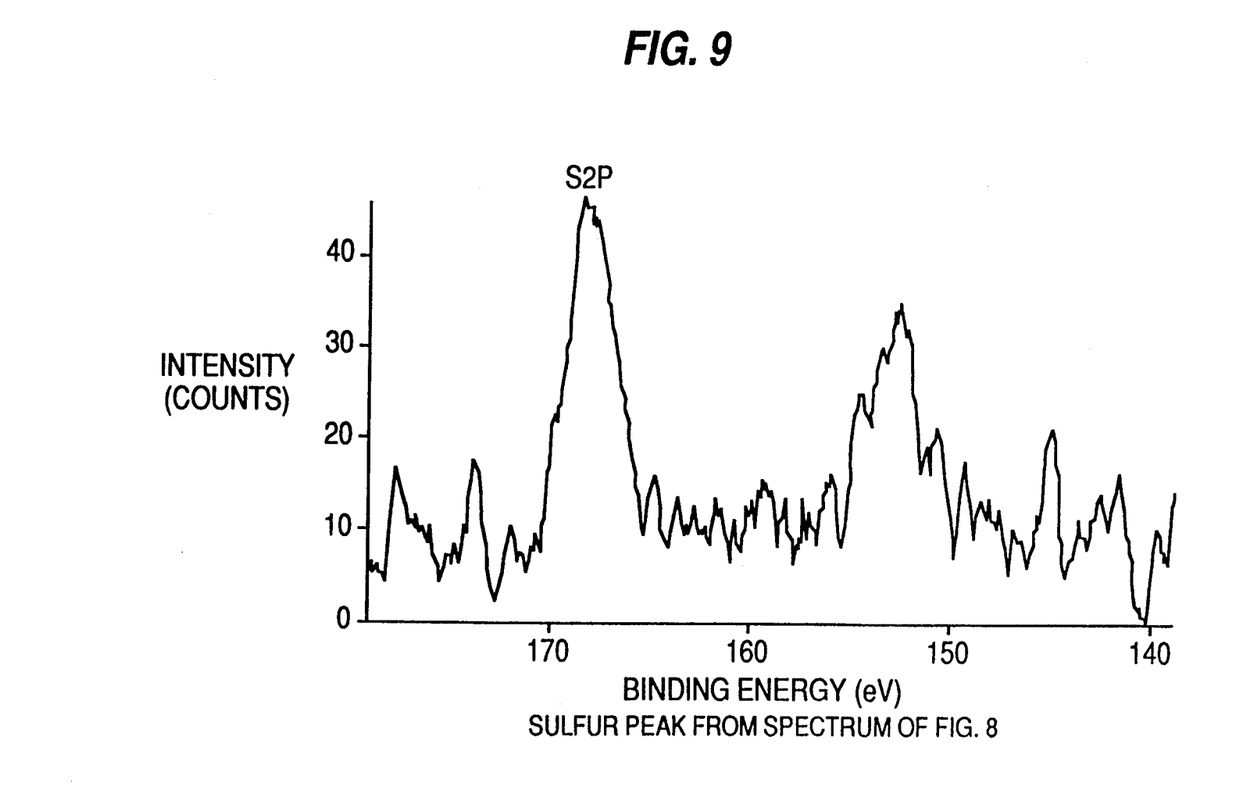

Surface characterization is carried out using air bubble contact angle and XPS analysis (FIG. 9).

TABLE 17

| | Data for PSSA-g-PMMA. | | | |
|---|---|---|---|---|
| | No Pre-soak | | Pre-soak: 40% NVP/ 60° C./4 hours | |
| | Wt. % Graft | C.A. (air) | Wt. % Graft | C.A. (air) |
| 20% Monomer (SSA) | <1 | 35° | 1 | 27° |
| 30% Monomer 2:1 (SSA:NVP) | <1 | 30° | 2 | 17° |
| 40% Monomer | <1 | 20° | 4 | 15° |

Figure 8:
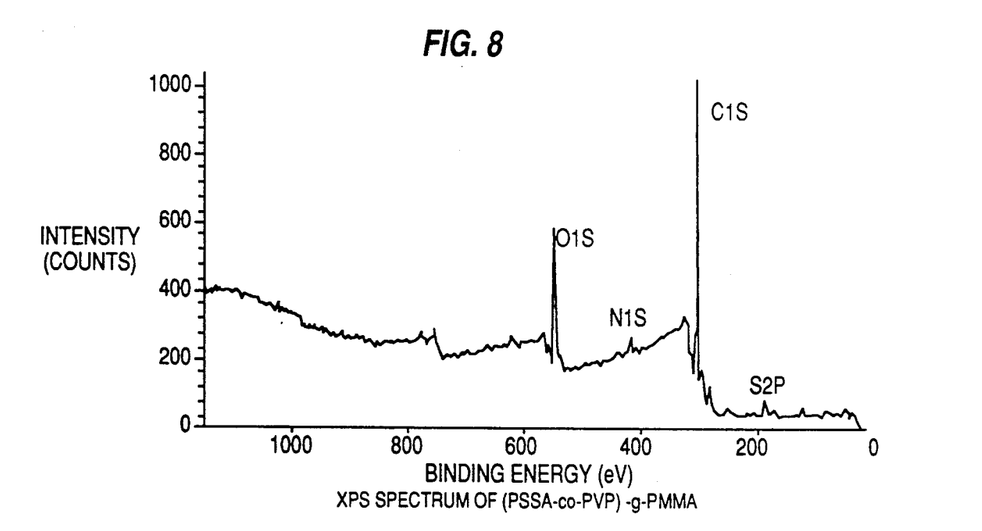

XPS analysis shows clear evidence of PSSA surface grafts (FIGS. 8 and 9).

EXAMPLE 10

Intraocular lenses (IOLs) are readily surface modified using conditions described in the above examples. Implants in rabbit eyes for periods of up to one year demonstrate the good bio-acceptance of the hydrophilic gamma polymerization surface modified IOL ocular implants prepared using the monomers and process conditions of this invention. For example, Sinskey-style-037 J-loop lenses (PMMA optics/PP haptics), surface modified using DMA, PEGMA and KSPA implanted in the anterior chambers, and one-piece flexible haptic PMMA IOLs implanted in the posterior chambers of New Zealand white rabbits show good biocompatibility. Process conditions for the pre-soak process improvement for IOL surface modifications are preferable.

Periodic slit lamp examinations of eyes, histopathology after one year and microscopic examination of explanted lenses (compared to ungrafted PMMA control IOLs), indicate good biocompatibility for the hydrophilic neutral and ionic polymer surface graft modifications of this invention.

EXAMPLE 11

This example demonstrates the large favorable effect of hydrophilic gamma graft surface modification on reducing tissue adhesion by measuring corneal endothelium adhesion and cell adhesion. These are important factors in demonstrating the improved biocompatibility and minimal tissue irritation or damage afforded by the hydrophilic graft surface modifications of this invention.

An apparatus which measures the force of adhesion (mg/cm$^2$) between contacting polymer and tissue surfaces is used to determine adhesion between rabbit corneal endothelium and polymer surfaces. Adhesion force values of about 250–400 mg/cm$^2$ were measured for PMMA and other hydrophobic polymers evaluated for implants, i.e., silicone, polypropylene, and the like. The improved hydrophilic gamma graft surfaces, prepared under preferred process conditions, exhibit much lower adhesion, below 150 mg/cm$^2$ and often less than 100 mg/cm$^2$. This is accompanied by a major reduction in endothelium cell damage as measured by SEM; from about 50–80% damage for hydrophobic PMMA, silicone, and the like to 20% or less for surfaces gamma grafted under preferred process conditions using the monomers of this invention.

The hydrophilic gamma graft surface modifications of this invention also show a major reduction in cell adhesion as demonstrated by exposure to live cell cultures of rabbit lens epithelial cells (LE). Experiments indicate that 2–4 times more LE cells adhere to PMMA or silicone as compared to the surface modified hydrophobic polymer substrates. Grafts prepared under the process conditions preferred often showed adherence of 0–1 cells/mm$^2$ compared to 10–25 cells/mm$^2$ for hydrophobic medical device polymers.

EXAMPLE 12

This example demonstrates the graft copolymerization of anionic or cationic monomers with the hydrophilic monomers of this invention using ionic monomers with NVP, DMA or PEGMA.

Using dimethylaminoethylacrylate, copolymerized with DMA or PEGMA, cationic graft coatings are prepared with C.A. <20°. Styrene sulfonic acid (SSA) was also used to produce anionic graft copolymers with NVP or PEGMA on PMMA and other device polymer substrates. For example, styrene sulfonic acid sodium salt (NaSSA) was used to prepare highly hydrophilic anionic copolymer grafts with NVP on silicones (PDMS). PDMS samples were cleaned by sonication in ethanol and vacuum dried prior to irradiation in aqueous monomer solutions. Table 18 lists grafting conditions, monomer concentrations and contact angles for graft surfaces prepared at a dose rate of about 700 rads/min.

TABLE 18

| Dose (Mrad) | % NaSSA | % NVP | C.A. |
|---|---|---|---|
| 0.05 | 20 | 20 | 17° |
| 0.10 | 20 | 20 | 15° |
| 0.15 | 20 | 20 | 13° |

As shown in Table 18, under conditions of even a relatively low total dose of 0.05 Mrad, using 40% total monomer and 50% anionic NaSSA comonomer, very hydrophilic (C.A. 17°) anionic grafts are achieved.

EXAMPLE 13

Hydrophilic Surface Modification of FEP Teflon Intravenous Catheter Polymers by DMA or PEGMA FEP teflon is a fluorocarbon polymer which is used for a number of medical devices such as intravenous catheters. It is very hydrophobic with a contact angle greater than 95° and shows significant tissue adhesion and damage on contact as indicated by in vitro rabbit corneal endothelium tests: about 250 mg/cm$^2$ adhesion force and 30–50% cells destroyed. FEP teflon film is surface modified using DMA or PEGMA by the following procedure to produce hydrophilic surfaces with contact angles less than 30°–40°, with low tissue adhesion and tissue damage reduced to less than 20%. For example, FEP films soaked in 20% aqueous monomer and irradiation to gamma doses of 0.10–0.20 Mrad yield hydrophilic graft surfaces with contact angles less than 35°. FEP intravenous catheters exhibit improved surface properties when hydrophilic surface modified by the materials and processes of this invention, i.e., reduced pain and insertion force, reduced vascular endothelium damage, improved blood compatibility and reduced susceptibility to adherence of pathogens and associated infections. Central venous catheters and heart catheters are also beneficially surface modified in this manner. Other fluorocarbon polymer catheters (e.g., PTFE) are similarly improved by this hydrophilic surface modification.

A further improvement in the gamma graft process for hydrophilic surface modification of fluorocarbon polymers is achieved through a surface pre-treatment with a defluorinating agent such as sodium naphthalene. For example, exposure of PTFE to a sodium naphthalene solution for only 30-60 seconds followed by gamma grafting of DMA or PEGMA results in grafts with improved wettability as compared with no pre-treatment and contact angles of 30° for 10% monomer solution and 0.1 Mrad. Copolymers with HEMA give hydrophilic grafts at monomer concentrations as low as 1% and gamma doses as low as 0.01 Mrad.

EXAMPLE 14

Hydrophilic Surface Modification of Porous PTFE Vascular Graft (Goretex TM) by Gamma-PVP Process Porous PTFE vascular grafts are pre-soaked in acetone, acetone-water-monomer solutions and then irradiated immersed in an aqueous monomer solution; typically 10% PEGMA, 5% acetone, 85% water in a gamma source to 0.02-0.15 Mrad total dose. After thorough washing with water, the PTFE has a hydrophilic surface modification with a major reduction in contact angle (from 98° unmodified to about 25° for the surface graft). The mechanical properties of the fluorocarbon polymer substrate are virtually unchanged by the very low gamma radiation doses required for hydrophilic polymer grafting. The surface modification is shown to have little effect upon the porous structure of the PTFE vascular graft by scanning electron microscopy.

The resulting hydrophilic surface modified PTFE and porous vascular graft materials exhibit improved blood compatibility properties of special value for small diameter vascular grafts and for other blood contacting implants and devices, i.e., heart valves, ventricular assists, artificial hearts, vascular catheters and pacer leads.

The very low doses of this invention do not damage or change the bulk properties of PTFE substrates and the use of low gamma doses with aqueous polymerization media results in very thin uniform hydrophilic surface modifications with retention of the substrate structure and physical properties, i.e., the pore structure of porous vascular graft PTFE materials.

EXAMPLE 15

DMA-HEMA Copolymer Gamma Graft on FEP Teflon

DMA-HEMA copolymer gamma grafting of FEP teflon is efficient at DMA:HEMA ratios of 9:1 and 8:2 yielding very hydrophilic surface modification with 10% aqueous monomer solutions and 0.05-0.1 Mrad (contact angles of 30° or less). Hydrophilic surface modified FEP teflon intravenous catheters are readily prepared by this method to yield catheters with reduced insertion force and pain, and which are less likely to exhibit i.v. catheter complications such as infection, phlebitis, clotting, and the like.

EXAMPLE 16

Surface Modification of Polyurethanes

Polyurethanes (PURs) have become increasingly important polymers for medical devices and implants, especially for i.v. catheters, pacer leads, vascular grafts and artificial heart applications. Although PURs are usually somewhat more hydrophilic than silicones or fluorocarbons, they do not generally exhibit the significant reduction in tissue adhesion and low tissue damage properties of more hydrophilic graft copolymer surface modifications of this invention. Improved surface properties for medical devices and implants is achieved using the monomers and the gamma irradiation surface modification process of this invention.

For example, a film of a 55 durometer polyurethane polyether block copolymer (Pellthane 5363) is gamma irradiated to 0.1 Mrad in oxygen degassed 10% aqueous PEGMA to yield significantly more hydrophilic surfaces. The unmodified contact angle of 54° is reduced to <30° for the surface modified PUR. In vitro endothelium contact damage tests for PURs yield cell damage results averaging 60% or more compared to cell damage of less than 20% which is found for the hydrophilic surface modifications. This improvement in PUR surface properties is especially important for commonly used radio-opaque PUR formulations containing such additives as barium sulfate because such formulations tend to have poorer biocompatibility. A typical PUR (Pellthane) formulation containing about 12% $BaSO_4$, for example, exhibits very high endothelium contact damage (80%) which is greatly reduced (<30%) by the hydrophilic polymer surface modifications of this invention.

It is conventional for many medical device polymers to be filled with barium or bismuth radio-opaque compounds (i.e., $BaSO_4$) to enable x-ray examination. This can make surfaces even more damaging to tissues. Surface modification according to the method of the present invention is especially beneficial for such radio-opaque polymer compositions to provide smoother, tissue-protective, more biocompatible surfaces.

EXAMPLE 17

Hydrophilic Surface Modified PMMA Contact Lenses

This example illustrates the beneficial tissue-protective properties obtained by hydrophilic polymer surface modification of conventional hard (PMMA) contact lenses. Such contact lenses are normally irritating and abrasive to the external corneal epithelium. PMMA contact lenses are surface modified by gamma graft polymerization immersed in aqueous PEGMA or DMA monomer (typically 10%) using 0.1 Mrad dose. The resulting transparent hydrophilic grafts make the contact lens surface water wettable (<30°C.A.) and non-adherent to the epithelial surface, thereby reducing epithelial abrasion and irritation. The various monomers and process improvements of this invention may be readily adapted to produce contact lenses with controlled surface modification thickness suited to specific patient needs.

EXAMPLE 18

Hydrophilic Surface Modified Silicone Soft Contact Lens

Silicone soft contact lenses are widely used due to their mechanical flexibility and good oxygen permeability. However, silicone is normally hydrophobic. It is, therefore, not water wettable and may adhere to or abrade sensitive corneal epithelial tissue. Many types of silicone contact lenses are surface-treated with an oxidizing plasma to increase water wettability and minimize this problem. However, this type of surface oxidation has only a slight tissue-protective value and is usually transient in aqueous media. The silicone surface loses its hydrophilicity and becomes less wettable, often with a few weeks. In contrast, the hydrophilic polymer surface grafts of this invention are permanently bound chemically and persist indefinitely to maintain excellent water wettability. Furthermore, they exhibit non-adherent, lubricious, tissue-protective qualities in contact with the corneal epithelium, thereby minimizing abrasion and irritation while retaining the favorable optical, mechanical and oxygen permeability properties of the polysiloxane.

Commercially available silicone contact lenses are readily surface modified using AM, DMA, PEGMA and ionic monomers of this invention. Typically, silicone contact lenses are gamma irradiated in 10% aqueous monomer to 0.1 Mrad to yield a hydrophilic surface modification with a C.A. less than 35° which is stable in aqueous media and which is significantly less irritating to the corneal epithelium. Certain ionic modifications are also less susceptible to protein, lipid and bacterial adsorption complications.

EXAMPLE 19

Hydrophilic Surface Modified Endotracheal Tubes and Cuffs

Endotracheal and tracheostomy tubes are conventionally made of silicones, polyurethanes, fluorocarbon polymers and polyvinyl chlorides. Balloons or cuffs on these airway devices are inflated during intubation and are usually made of latex rubber, vinyl or silicone polymers. Significant clinical problems associated with the use of these devices are desquamation of the ciliated cells of the trachea and even more severe damage to the trachea due to the pressure, irritation and adhesion of the cuffs. Post-operative infections are associated with adherence of pathogens to the damaged and denuded areas of the trachea caused by the airway tube cuff. Hydrophilic polymer surface modification of the tube and cuff surfaces according to this invention affords a significant improvement in these devices by minimizing abrasive contacts and adhesion to the sensitive tracheal tissues.

A silicone cuff is modified by PEGMA-HEMA (10:1) by the method of Example 18. The resulting hydrophilic cuff has markedly reduced adhesion to tissue and causes less tracheal irritation and damage than hydrophobic polysiloxane cuffs. Similarly, a latex rubber cuff is modified by gamma grafted PVP according to the method of Example 18. The resulting hydrophilic cuff is less adherent to sensitive tracheal tissue than normal hydrophobic latex rubber cuffs causing less tracheal irritation and damage during intubation.

EXAMPLE 20

Hydrophilic Surface Modification of Foley Catheter Tubes and Balloons

Foley catheter tubes and balloons are used for catheterization of the urinary tract and conventionally made of the same hydrophobic polymers used for endotracheal tubes and cuffs as noted in Example 19. Clinical complications associated with such devices are tissue irritation, infection and encrustation due to the tissue adherent and damaging surface properties of the hydrophobic catheters and the adherence of pathogens, proteins and minerals to the surfaces. Although silicone and fluorocarbon polymers tend to exhibit reduced mineral deposits and encrustation, hydrophilic polymer surface modification affords improved resistance to the problems of tissue irritation, infection and encrustation.

A silicone Foley catheter is modified by DMA. PEGMA and ionic copolymers according to the method of Example 18. The resulting hydrophilic surface modified catheters have reduced tissue adhesion and exhibit less encrustation than unmodified silicone. In another example of the advantages of this invention, a Foley catheter with a latex balloon is surface modified using these monomers yielding hydrophilic surfaces which are less likely to promote infection and are less susceptible to encrustation.

EXAMPLE 21

Hydrophilic Surface Modification of Surgical Gloves and Sponges

Latex rubber surgical gloves exhibit hydrophobic surface properties and tend to adhere to sensitive tissue surfaces, thereby enhancing manipulative damage to tissues in all types of surgery. Manipulative damage can result in increased post-operative complications such as infection and surgical adhesions. Hydrophilic surface modification of surgical gloves results in reduced tissue adhesion of the rubber latex and less chance of severe manipulative tissue trauma due to contact with gloves. Latex rubber gloves are surface modified with hydrophilic AM or DMA surfaces using the process of this invention making it feasible to accomplish this hydrophilic polymer grafting without altering the mechanical properties of the radiation sensitive rubber latex. The resulting hydrophilic latex surgical gloves are less adherent and less damaging to sensitive tissue normally contacted during surgery, i.e., peritoneum, pericardium, and the like.

Surgical sponges and gauzes used in surgical procedures are also damaging to tissue due to tissue adhesion and abrasion. Sponges and gauzes are normally made of cotton, polyester, cellulosic material and polyurethanes. These natural and synthetic polymers are all amenable to hydrophilic surface modification by the materials and processes of this invention. In a typical example, a cotton gauze sponge is surface modified by gamma grafting with PEGMA using 10% aqueous monomer and 0.1 Mrad dose. The sponge surface is thereby rendered more hydrophilic and less abrasive to tissue during surgical manipulation without altering the structure and function of the sponge.

EXAMPLE 22

Hydrophilic Surface Modification of Silicone Mammary Prosthesis

Mammary prostheses are most commonly constructed of a hydrophobic polysiloxane skin or membrane containing air, water or silicone gels or fluids. A major complication of such soft tissue prostheses is the irritation and inflammatory process which occurs at the tissue-implant interface which leads to formation of a hard fibrous capsule surrounding the implant. This fibrous capsule can severely compromise the bio-acceptance of the prosthesis and, if severe, can lead to tissue necrosis, extrusion and loss of the implant. The hydrophilic surface modification of the silicone which is accomplished by this invention leads to reduced tissue irritation and abrasion by the implant and reduced adhesion of infiltrating cells during the post-operative period which normally can lead to extensive fibrous capsule formation. A silicone bag/silicone gel mammary prosthesis is surface modified with a hydrophilic PEGMA or DMA graft according to the method of Example 18 or preferably using a pre-soak process with an initial PVP graft followed by PEGMA grafting. This hydrophilic prosthesis surface is less adherent to tissue or cells as compared to normal silicone and thereby has improved biocompatibility with less tendency to form a surrounding hard fibrous capsule.

EXAMPLE 23

Hydrophilic Surface Modification of Carbon Fiber Composite Reinforced Polycarbonate Surgical Instrument Plastic surgical instruments made of various hydrophobic structural polymers are used to an increasing extent because plastics lend themselves to high-quality/low-cost manufacture of special value for disposable instruments. Such instruments may exhibit significant tissue adhesion with accompanying manipulative trauma. Improved tissue protective properties are achieved by the hydrophilic polymer surface modification of this invention. Fiber reinforced composites are among the most important examples of plastic materials used for instruments (containing glass, carbon or boron fibers to provide rigidity and high mechanical strength). Carbon fiber reinforced bisphenol-A polycarbonate microsurgical forceps for surgical insertion of an ocular implant is an example of a surgical instrument which is significantly improved by this invention. Using the process of Example 2 for the polycarbonate polymer, the carbon fiber reinforced polycarbonate instrument is readily surface modified with AM or DMA. The resulting instrument surface is much less adherent to tissue and less damaging in contacts with fragile ocular tissues. Additionally, the surface modified plastic instrument is less likely to scratch or damage the surface of plastic implants.

EXAMPLE 24

Hydrophilic Surface Modification of Silicone Irrigation/Aspiration (I/A) Tools Used in Ophthalmic Surgery In ophthalmic surgery, I/A tools are used to irrigate the eye with irrigating solutions and to aspirate fluids and tissue debris out of the eye. Silicone tips are commonly used on such I/A instruments. They are maneuvered around the anterior and posterior chambers of the eye with resulting frequent contacts with fragile tissues. For hydrophobic silicone devices, these tissue contacts may cause significant tissue damage which can compromise the success of the ocular surgery.

Silicone I/A tips are surface modified with DMA and DMA-HEMA by the processes of this invention. The resulting hydrophilic polymer surface is less adherent to tissue and less damaging on contact with sensitive tissues during surgery.

EXAMPLE 25

Hydrophilic Surface Modification of Polyurethane Artificial Heart

Implants or ex-vivo heart assist and artificial heart devices are most often constructed of woven fiber reinforced segmented polyether polyurethanes because of their superior mechanical strength properties. However, these materials are still thrombogenic to a significant degree and clotting complications severely limit the use of such devices. Modification of the surfaces of such devices with hydrophilic polymer grafts which are less thrombogenic by virtue of low blood cell and platelet adhesion and activation, low fibrinogen adsorption, and the like, is efficacious in prolonging the useful life of such devices and implants. A polyurethane Jarvic-7-type artificial heart is readily surface modified with a PEGMA graft by the process of Example 16. The process of the invention is uniquely suitable for the uniform hydrophilic surface modification of highly irregular complex structures such as the artificial heart since the entire device is immersed in the monomer solution and radiation permeates the entire structure to uniformly activate the substrate and initiate surface graft polymerization in a controlled manner.

EXAMPLE 26

Hydrophilic Surface Modification of Polyvinylchloride (PVC) Catheters

PVC is widely used for catheters, blood tubing, blood bags and many other medical devices. Formulations are hydrophobic and exhibit some adverse tissue adhesion and cell adhesion behavior. Hydrophilic surface modification is useful in improving blood and tissue compatibility. Since formulations often contain significant concentrations of plasticizers (i.e., dioctyl phthalate), leaching of surface plasticizer by washing with appropriate solvents such as aqueous acetone prior to gamma graft surface modification is preferred. After aqueous acetone washing, a PVC vascular catheter is exposed to 0.1 Mrad immersed in degassed 10% aqueous DMA to yield a hydrophilic graft which exhibits less vascular endothelium damage on contact and which is less thrombogenic than unmodified PVC.

EXAMPLE 27

Hydrophilic Grafting of Medical Devices Having Combinations of Materials

One of the important aspects of this invention is the discovery that certain grafting process conditions make it feasible to surface modify combinations of materials to be used in medical devices. Surface grafting of an assembled device can then take place in a one-step simultaneous grafting procedure yielding improved, more biocompatible surfaces. Materials combinations of PMMA, PC, PUR, fluorocarbons, PP, PDMSO and other polymers can thereby be grafted under conditions of this invention. The following are some device combinations with mutual grafting conditions for obtaining improved PEGMA or DMA grafts.

PMMA/PP and PMMA/PVDF

PMMA and PP gamma graft under degassed conditions at 157 rads/min, 0.05 Mrad, 10% monomer to yield grafts with contact angles of <25° which are mechanically stable. Non-degassed PP generally grafts less efficiently than PMMA because of the adverse effect oxygen has on PP surface grafting.

PVDF surface grafts are also favored by oxygen degassing. A 10% degassed aqueous monomer solution, irradiated at 157 rads/min to 0.05 Mrad, gives hydrophilic grafts on both PMMA and PVDF.

PC/PP and PC/PVDF

PC and PP graft under similar pre-soak gamma irradiation process conditions when monomer solutions of this invention are degassed using 157 rads/min. and 0.05–0.1 Mrad.

We claim:

1. A method for modifying a plastic surface of an article, said surface adapted for contact with living tissue of a human or non-human animal, by the gamma irradiation induced polymerized chemically grafted coating thereon of:
  (1) a neutral or ionic water-soluble, hydrophilic, vinylic monomer or salt thereof;
  (2) a mixture of at least two of said monomers, or
  (3) a mixture of (1) or (2) with up to about 50%, by weight, based on the total monomer weight, of a member selected from the group consisting of N-vinylpyrrolidone, 2-hydroxyethyl-methacrylate, and mixtures thereof; so as to form a hydrophilic graft polymer coating on said surface comprising:
  conducting said gamma irradiation induced graft polymerization in an aqueous solution under the following conditions:
  a) total monomer concentration in the range of from about 0.1% to about 50%, by weight;
  b) total gamma dose in the range of from about 0.001 to less than about 0.50 Mrad; and
  c) gamma dose rate in the range of from about 10 to about 2,500 rads/min.

2. The method of claim 1 further including one or more of the following conditions:
  d) degassing free oxygen from said graft polymerization solution;
  e) maintaining the thickness of said polymer coating in the range of from about 100 Å to about 100 microns;
  f) including a free radical scavenger in said aqueous graft polymerization solution; and
  g) including in said aqueous graft polymerization solution a swelling solvent for said plastic surface.

3. The method of claim 1 or 2 wherein said monomer is selected from the group consisting of acrylamide, dimethylacrylamide, polyethylene glycol monomethacrylate, hydroxypropylacrylamide, methacrylic acid, sulfopropylacrylate, styrene-sulfonic acid, 2-acrylamide-2-methyl-1-propane sulfonic acid, vinylsulfonic acid, dimethylaminoethylmethacrylate, mixtures and salts thereof.

4. The method of claim 1 or 2 further including, prior to said step of polymerization, the step comprising pre-soaking said plastic surface in at least one of said monomers (1) or (3) or in a first aqueous solution of at least one of said monomers (1) or (3), having a concentration of monomer therein of from about 5 to about 95%, by weight; said pre-soaking being conducted for a period of time and at a temperature sufficient to facilitate diffusion of said monomer into said plastic surface.

5. The method of claim 4 wherein said pre-soaking step is conducted at a temperature in the range of from about 25° to about 90° C. and for a period of time of from about 0.5 to about 48 hours.

6. The method of claim 1 wherein said article is an ocular implant material.

7. The method of claim 1 wherein said article is a surgical instrument.

8. The method of claim 1 wherein said article is a medical device.

9. The method of claim 1 wherein said article is a prosthetic implant.

10. The method of claim 1 wherein said article is a soft or hard contact lens.

11. The method of claim 1 wherein said plastic is selected from the group consisting of polyacrylates, polymethacrylates, polyolefins, styrene-butadiene copolymers, styrene-ethylene-butadiene copolymers, polycarbonates, fluorocarbon polymers, polysiloxanes, polyurethanes, polyvinylchloride, polyesters, mixtures, and copolymers thereof.

12. The method of claim 11 wherein said polyolefin is an ethylene-propylene copolymer or polybutadiene.

13. A method for modifying a plastic surface of an article, said surface adapted for contact with living tissue of a human or non-human animal, by the one-step electron beam-irradiation induced polymerized chemically grafted coating thereon of:
  (1) a neutral or ionic water-soluble, hydrophilic, vinylic monomer or salt thereof;
  (2) a mixture of at least two of said monomers, or
  (3) a mixture of (1) or (2) with up to about 50%, by weight, based on the total monomer weight, of a member selected from the group consisting of N-vinylpyrrolidone, 2-hydroxyethyl-methacrylate, and mixtures thereof; so as to form a hydrophilic graft polymer coating on said surface comprising:
  conducting said electron beam-irradiation induced graft polymerization in an aqueous solution of at least one of said monomers under the following conditions:
  (a) monomer concentration in the range of from about 0.1% to about 50%, by weight;
  (b) total electron beam irradiation dose equivalent to a gamma irradiation dose in the range of from about 0.001 to less than about 0.50 Mrad; and
  (c) an electron beam irradiation dose rate equivalent to a gamma irradiation dose rate in the range of from about 10 to about $10^8$ rads/min.

14. The method of claim 13 further including, prior to said step of polymerization, the step comprising: pre-soaking said plastic surface in at least one of said monomers (1) or (3) or in a first aqueous solution of at least one of said monomers (1) or (3), having a concentration of monomer therein of from about 5 to about 95%, by weight, said pre-soaking being conducted for a period of time and at a temperature sufficient to facilitate diffusion of said monomer into said plastic surface.

15. The method of claim 13 or 14 wherein said monomer is selected from the group consisting of acrylamide, dimethylacrylamide, polyethylene glycol monomethacrylate, hydroxypropylacrylamide, methacrylic acid, sulfopropylacrylate, styrene-sulfonic acid, 2-acrylamide-2-methyl-1-propane sulfonic acid, vinylsulfonic acid, dimethylaminoethylmethacrylate, mixtures and salts thereof.

16. An article prepared according to the method of claim 1 or 13.

17. An article according to claim 16 comprising a surgical instrument, medical device, prosthetic implant, contact lens or ocular implant.

* * * * *